US011079365B2

United States Patent
Nam et al.

(10) Patent No.: US 11,079,365 B2
(45) Date of Patent: Aug. 3, 2021

(54) SPECTRUM SIMULATION APPARATUS AND METHOD FOR CONTAMINATED ATMOSPHERE

(71) Applicant: AGENCY FOR DEFENSE DEVELOPMENT, Daejeon (KR)

(72) Inventors: Hyunwoo Nam, Daejeon (KR); Jongseon Kim, Daejeon (KR); Hyeonjeong Kim, Daejeon (KR); Youngjin Koh, Daejeon (KR)

(73) Assignee: AGENCY FOR DEFENSE DEVELOPMENT, Daejeon (KR)

( * ) Notice: Subject to any disclaimer, the term of this patent is extended or adjusted under 35 U.S.C. 154(b) by 0 days.

(21) Appl. No.: 16/743,346

(22) Filed: Jan. 15, 2020

(65) Prior Publication Data
US 2021/0096118 A1  Apr. 1, 2021

(30) Foreign Application Priority Data
Sep. 27, 2019  (KR) .................. 10-2019-0119971

(51) Int. Cl.
*G01N 21/3504*  (2014.01)
*G01N 33/00*  (2006.01)
(Continued)

(52) U.S. Cl.
CPC ..... *G01N 33/0062* (2013.01); *G01N 21/3504* (2013.01); *G06T 7/70* (2017.01);
(Continued)

(58) Field of Classification Search
CPC .. G01N 33/0062; G01N 21/3504; G06T 7/90; G06T 7/70; G06T 11/001; G06T 2207/10048
(Continued)

(56) References Cited

U.S. PATENT DOCUMENTS

2004/0153300 A1* 8/2004 Symosek ........... G01N 33/0006
  703/11
2017/0052643 A1* 2/2017 Iwami .................. G06F 3/0418

FOREIGN PATENT DOCUMENTS

KR  20110126974 A  11/2011
KR  101589619 B1  1/2016
(Continued)

OTHER PUBLICATIONS

Lee et al., Field identification and spatial determination of hazardous chemicals by Fourier transform infrared imaging, Instrumentation Science and Technology, vol. 44, No. 5, 504-520 (Year: 2016).*
(Continued)

*Primary Examiner* — Toan M Le
*Assistant Examiner* — Xiuqin Sun
(74) *Attorney, Agent, or Firm* — Scully Scott Murphy and Presser

(57) ABSTRACT

Provided is a simulation spectrum apparatus including: a background image acquisition unit that acquires a background image of a target region and an infrared signal corresponding to each pixel of the background image; a spectrum acquisition unit that acquires a background radiation intensity spectrum from the infrared signal acquired for the each pixel; a simulation spectrum generation unit that generates a model of a linear combination of a radiation intensity spectrum of a contamination cloud and a background radiation intensity spectrum on the basis of a difference in radiation intensity; a controller that generates a simulation spectrum of the contamination cloud by applying the information on the at least one toxic substance and the atmosphere transmittance to the model of the linear combination; and an imaging unit that generates a spectrum image, combines the generated spectrum image and the background image, and thus generates a simulation contamination cloud image.

16 Claims, 9 Drawing Sheets

(51) Int. Cl.
    *G06T 7/90* (2017.01)
    *G06T 7/70* (2017.01)
    *G06T 11/00* (2006.01)

(52) U.S. Cl.
    CPC .............. *G06T 7/90* (2017.01); *G06T 11/001* (2013.01); *G06T 2207/10048* (2013.01)

(58) Field of Classification Search
    USPC .......................................................... 702/24
    See application file for complete search history.

(56) References Cited

FOREIGN PATENT DOCUMENTS

| KR | 101626370 | B1 | 6/2016 |
|---|---|---|---|
| KR | 20160113899 | A | 10/2016 |
| KR | 101768107 | B1 | 8/2017 |
| KR | 20180097353 | A | 8/2018 |

OTHER PUBLICATIONS

Harig et al., Remote measurement of highly toxic vapors by scanning imaging Fourier transform spectrometry, SPIE, Optics East 2005, Boston, MA, United States (Year: 2005).*
Google scholar search results, Mar. 24, 2021, 4 pp. (2019).*
NPL search results, Mar. 24, 2021, 2 pp. (2021).*
Nam, Hyunwoo et al., "Development of a radiative transfer model for the determination of toxic gases by Fourier transform-infrared spectroscopy with a support vector machine algorithm", Instrumentation Science & Technology (2019), vol. 47, No. 3, pp. 264-277 (partial contents of present application).
Grant of Patent dated Feb. 19, 2020 issued in Korean Patent Application No. 10-2019-0119971 together with an English language translation.

* cited by examiner

FIG. 5
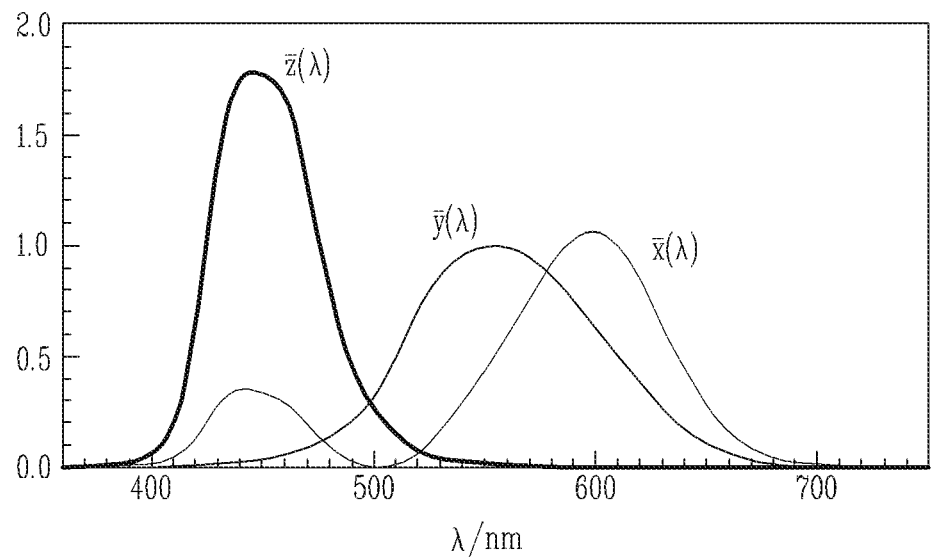
(a)
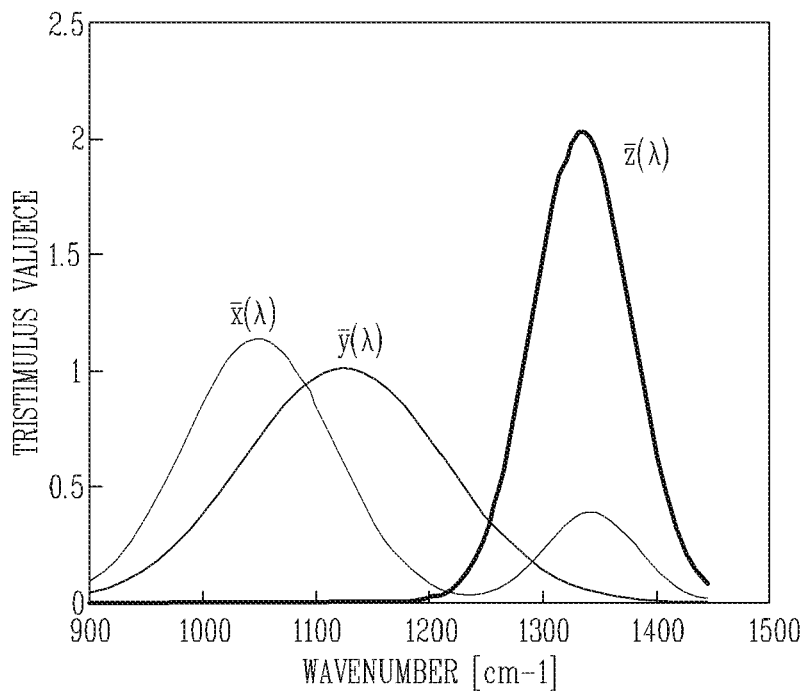
(b)

FIG. 6
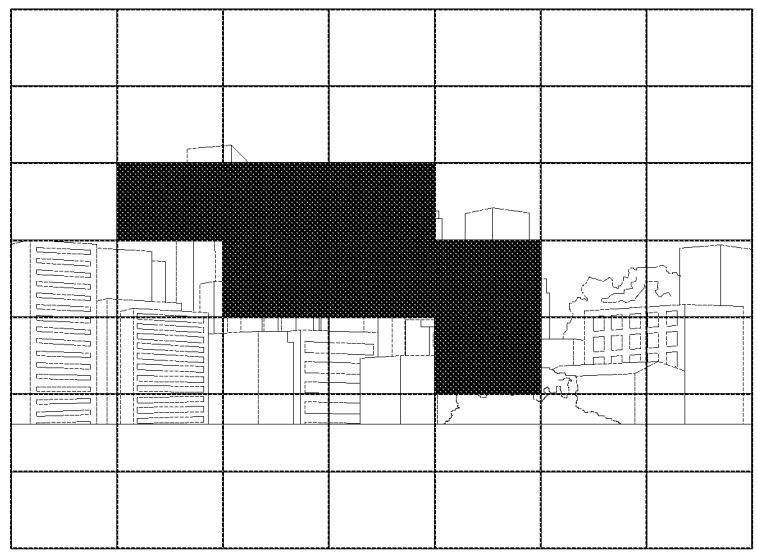
(a)
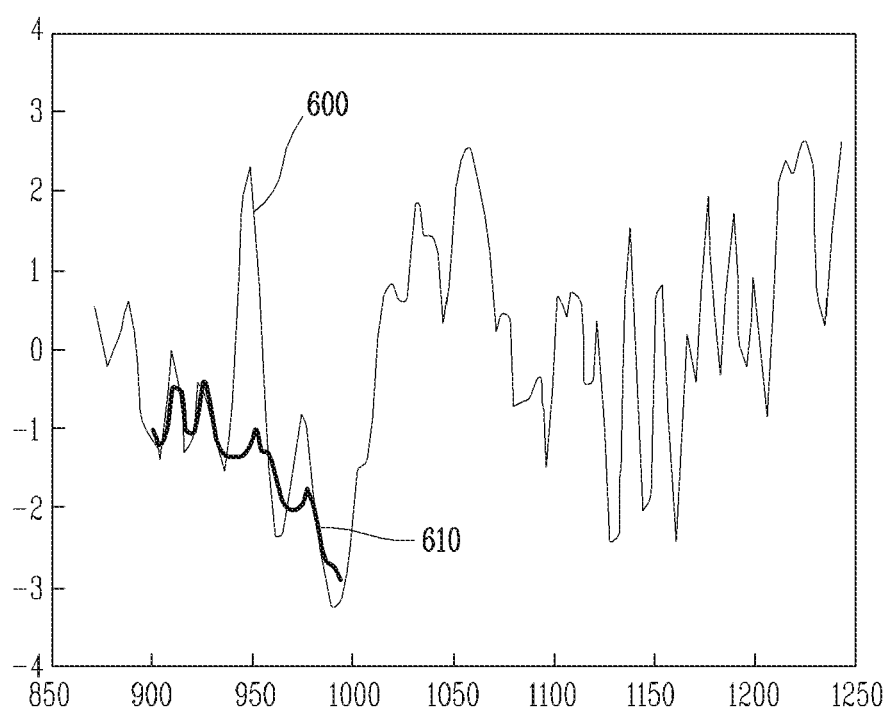
(b)

SPECTRUM SIMULATION APPARATUS AND METHOD FOR CONTAMINATED ATMOSPHERE

CROSS-REFERENCE TO RELATED APPLICATION

Pursuant to 35 U.S.C. § 119(a), this application claims the benefit of the earlier filing date and the right of priority to Korean Patent Application No. 10-2019-0119971, filed on Sep. 27, 2019, the contents of which is incorporated by reference herein in its entirety.

BACKGROUND

1. Technical Field

The present disclosure is intended to remotely detect and analyze toxic substances such as toxic chemical gas, and, more particularly, to simulate a ultraviolet hyper-spectral imaging spectrum signal of atmospheric gas contaminated with a toxic substance and analyze performance of detection algorithms.

2. Description of the Related Art

The accident in which leakage of a chemical warfare agent (CWA), such as a nerve agent, a blister agent, or a blood agent, that is used for the purpose of a terror, and a toxic industrial chemical (TIC) that is used in a chemical industrial complex takes place, inflicts death or harm on many people in a short period of time. Therefore, in order to minimize this infliction, there is a need to develop an early warning system for remotely detecting and identifying the leakage as soon as possible.

As this remote chemical gas detection technology, an infrared spectroscopy based on a Fourier-transform infrared (FT-IR) spectroscopy is widely used. The FT-IR-based remote detection technology is a technology that determines whether or not an atmospheric layer is contaminated, according to a result of comparing a spectrum characteristic of infrared light received from various natural backgrounds with a spectrum characteristic of the atmospheric layer contaminated with a contamination substance.

In this manner, in order to identify whether or not the atmospheric layer is contaminated and the toxic substance that contaminates the atmospheric layer, there is a need to analyze spectrums that are reflected from various backgrounds such as a forest, a sea, a sky, and a building, pass through the atmospheric layer contaminated with the toxic substance, and are collected.

For the purpose of performing this analysis, in Czechoslovakia, a sealed outdoor gas injection facility was constructed to collect spectrum characteristics of a comparative group for detecting toxic substances. Then, a toxic substance is sprayed outdoors through the constructed facility, and pieces of spectrum data on the atmospheric layer contaminated with the sprayed toxic substance are collected. Thus, a spectrum characteristic database on the comparative group is generated. However, a spectrum characteristic of the atmospheric layer appears in a manner that varies from one area to another due to climatic characteristics, which depend on an altitude or latitude of the corresponding area, or due to various environmental influences, such as an ambient ecological system. Therefore, there is a problem in that pieces of spectrum data collected in Czechoslovakia are difficult to apply domestically.

In addition, a large-sized chamber equipped with the outdoor safety facility has not yet been constructed domestically. The current situation is that construction of the large-sized chamber equipped with the safety facility creates huge costs. Accordingly, the spectrum characteristic database on the comparative group is difficult to build up domestically. There is a problem in that the reliability of remote toxic substance detection is decreased greatly due to this difficulty.

SUMMARY

An object of the present disclosure is to provide an apparatus and a method that are capable of simulating infrared hyper-spectral imaging spectrum characteristic data on the atmosphere contaminated with various toxic substances without contaminating the atmosphere using the toxic substances.

Another object of the present disclosure is to provide an apparatus and a method that are capable of visually analyzing performance of various chemical gas detection algorithms by utilizing a simulated spectrum and thus imaging a contamination cloud contaminated with a chemical agent.

According to an aspect of the present disclosure, there is provided a simulation spectrum apparatus including: a background image acquisition unit that includes at least one camera and an infrared sensor and acquires a background image of a target region and an infrared signal corresponding to each pixel of the background image; a spectrum acquisition unit that acquires a background radiation intensity spectrum from the infrared signal acquired for the each pixel; an input unit into which information on at least one toxic substance and atmosphere transmittance that are desired to be simulated are input; a simulation spectrum generation unit that generates a model of a linear combination of a radiation intensity spectrum of a contamination cloud and a background radiation intensity spectrum on the basis of a difference in radiation intensity, which depends on whether or not the contamination cloud is present; a controller that controls the simulation spectrum generation unit in such a manner that a simulation spectrum of the contamination cloud contaminated with the at least one toxic substance, which corresponds to the each pixel, is generated by applying the information on the at least one toxic substance and the atmosphere transmittance to the model of the linear combination; and an imaging unit that, under the control of the controller, generates a spectrum image in accordance with the simulation spectrum corresponding to the each pixel, combines the generated spectrum image and the background image, and thus generates a simulation contamination cloud image.

In the spectrum simulation apparatus, the simulation spectrum generation unit may make division into three phases, an atmosphere, a contamination cloud, and a background, and, on the basis of a three layers-based spectrum model that models a spectroscopic signal and the acquired background radiation intensity spectrum, may model a first spectrum model for a case where the contamination cloud is present and a second spectrum model for a case where the contamination cloud is not present, and the simulation spectrum generation unit may linearly combine a result of approximating a contamination cloud function, which results from approximating the atmosphere transmittance of the contamination cloud using a preset approximation method, and a difference between black-body radiation intensity of the contamination cloud and radiation intensity of the background, and the second spectrum model, and thus may generate the model of the linear combination.

In the spectrum simulation apparatus, the imaging unit may calculate a brightness temperature spectrum on the basis of the simulation spectrum corresponding to each pixel, may decide a color value for each pixel according to the calculated brightness temperature spectrum, and thus may generate the spectrum image.

In the spectrum simulation apparatus, the imaging unit may calculate a tristimulus value for the brightness temperature spectrum calculated for each pixel according to a tristimulus value function, may calculate a RGB value for each pixel according to the calculated tristimulus value, and may generate the spectrum image in which a color of each pixel is decided according to the calculated RGB value.

In the spectrum simulation apparatus, the imaging unit may calculate a YCbCR value corresponding to the RGB value calculated for each pixel and may generate the spectrum image in which the color of each pixel is decided according to the calculated YCbCR value.

The spectrum simulation apparatus may further: a memory that includes pieces of information on multiple detection algorithms; and an algorithm performance analysis unit that performs toxic substance detection for each of the multiple detection algorithms on the generated simulation cloud image under the control of the controller.

In the spectrum simulation apparatus, when at least one of the multiple detection algorithms is selected, the controller may control the algorithm performance analysis unit in such a manner that the generated simulation contamination cloud image is input into the selected detection algorithm and that a result of toxic substance detection in accordance with the selected algorithm is derived, and the controller may control the imaging unit, may image the result of the toxic substance detection, may perform comparison with the imaged result of the toxic substance detection, and may analyze performance of the selected detection algorithm.

In the spectrum simulation apparatus, with respect to the total number of pixels of the simulation contamination cloud image, the controller may analyze quantified performance of the selected detection algorithm according to the number of pixels in an imaged result of toxic substance detection, which are matched, in terms of the presence or absence of the toxic substance, with pixels of the simulation contamination cloud image.

In the spectrum simulation apparatus, the controller may analyze performance of the detection algorithm on the basis of an imaged result of toxic substance detection, and a receiver operating characteristic (ROC) analysis technique for the simulation contamination cloud image.

The spectrum simulation apparatus may further include an output unit that outputs the simulation contamination cloud image that results from the imaging in the imaging unit, or an imaged result of the toxic substance detection through the detection algorithm, as visual information.

According to another aspect of the present disclosure, there is provided a spectrum simulation method including: a first step of including at least one camera and an infrared sensor and acquiring a background image of a target region and an infrared signal corresponding to each pixel of the background image; a second step of acquiring a background radiation intensity spectrum from the infrared signal acquired for the each pixel; a third step of generating a model of a linear combination of a radiation intensity spectrum of a contamination cloud and a background radiation intensity spectrum on the basis of a difference in radiation intensity, which depends on whether or not the contamination cloud is present; a fourth step of generating a simulation spectrum of the contamination cloud contaminated with the at least one toxic substance, which corresponds to the each pixel, by applying the information on the at least one toxic substance and the atmosphere transmittance, which are input, to the model of the linear combination, when the information on the at least one toxic substance and the atmosphere transmittance that are desired to be simulated are input; and a fifth step of generating a spectrum image in accordance with the simulation spectrum corresponding to the each pixel, combining the generated spectrum image and the background image, and thus generating a simulation contamination cloud image.

In the spectrum simulation method, the third step may include a (3-1)-th step of making division into three phases, an atmosphere, a contamination cloud, and a background and modeling a first spectrum model for a case where the contamination cloud is present and a second spectrum model for a case where the contamination cloud is not present, on the basis of a three layers-based spectrum model that models a spectroscopic signal and the acquired background radiation intensity spectrum; and a (3-2)-nd step of linearly combining a result of approximating a contamination cloud function, which results from approximating the atmosphere transmittance of the contamination cloud using a preset approximation method, and a difference between black-body radiation intensity of the contamination cloud and radiation intensity of the background, and the second spectrum model and thus generating the model of the linear combination.

In the spectrum simulation method, with the spectrum image, a brightness temperature spectrum may be calculated on the basis of the simulation spectrum corresponding to each pixel, and a color value for each pixel may be decided and generated according to the calculated brightness temperature spectrum.

The spectrum simulation method may further include: an a step of selecting at least one of preset multiple detection algorithms; a b step of inputting the generated simulation contamination cloud image into the selected detection algorithm and deriving a result of toxic substance detection in accordance with the selected algorithm; a c step of imaging the derived result of the toxic substance detection; and a d step of performing a comparison with the imaged result of the toxic substance detection and analyzing performance of the selected detection algorithm.

In the spectrum simulation method, the d step may be a step of analyzing quantified performance of the selected detection algorithm according to the number of pixels in the imaged result of toxic substance detection, which are matched, in terms of the presence or absence of the toxic substance, with pixels of the simulation contamination cloud image, with respect to the total number of pixels of the simulation contamination cloud image.

In the spectrum simulation method, the d step may be a step of analyzing performance of the selected detection algorithm on the basis of the imaged result of the toxic substance detection, and a receiver operating characteristic (ROC) analysis technique for the simulation contamination cloud image.

BRIEF DESCRIPTION OF THE DRAWINGS

FIG. 5 is a diagram illustrating examples of a tristimulus value function for generating the simulation contamination cloud image in the spectrum simulation apparatus according to the embodiment of the present disclosure.

FIG. 6 is a diagram illustrating an example of a simulated contamination cloud image in the spectrum simulation apparatus according to the embodiment of the present disclosure.

DETAILED DESCRIPTION OF THE EMBODIMENTS

Notably, technical terms used in the present specification are only for describing specific embodiments and are not intended to impose any limitation on the scope of the present disclosure. In addition, the term used in the present specification, although expressed in the singular, is construed to have a plural meaning, unless otherwise meant in context. The phrase "is configured with," "include," or the like, which is used in the present specification, should not be construed as being used to necessarily include all constituent elements or all steps that are described in the specification, and should be construed in such a manner that, among all the constituent elements or among all the steps, one or several constituent elements or one or several steps, respectively, may not be included, or that one or several other constituent elements, or one or several other steps may be further included.

In addition, in a case where it is determined that a detailed description of the well-known technology in the relevant art to which the present disclosure pertains makes indefinite the nature and gist of the technology disclosed in the present disclosure, the detail description thereof is omitted from the present specification.

Unless otherwise defined, all terms including technical or scientific terms, which are used in the present specification, have the same meanings as are normally understood by a person of ordinary skill in the art to which the present disclosure pertains.

In addition, in the following description, an infrared section that is a major region of a toxic substance is defined as a region of interest. As an example, simulation of a spectrum in the region of interest will be described.

A spectrum simulation apparatus and a spectrum simulation method according to an embodiment of the present disclosure will be described in detail below with reference to the accompanying drawings.

Figure 1:
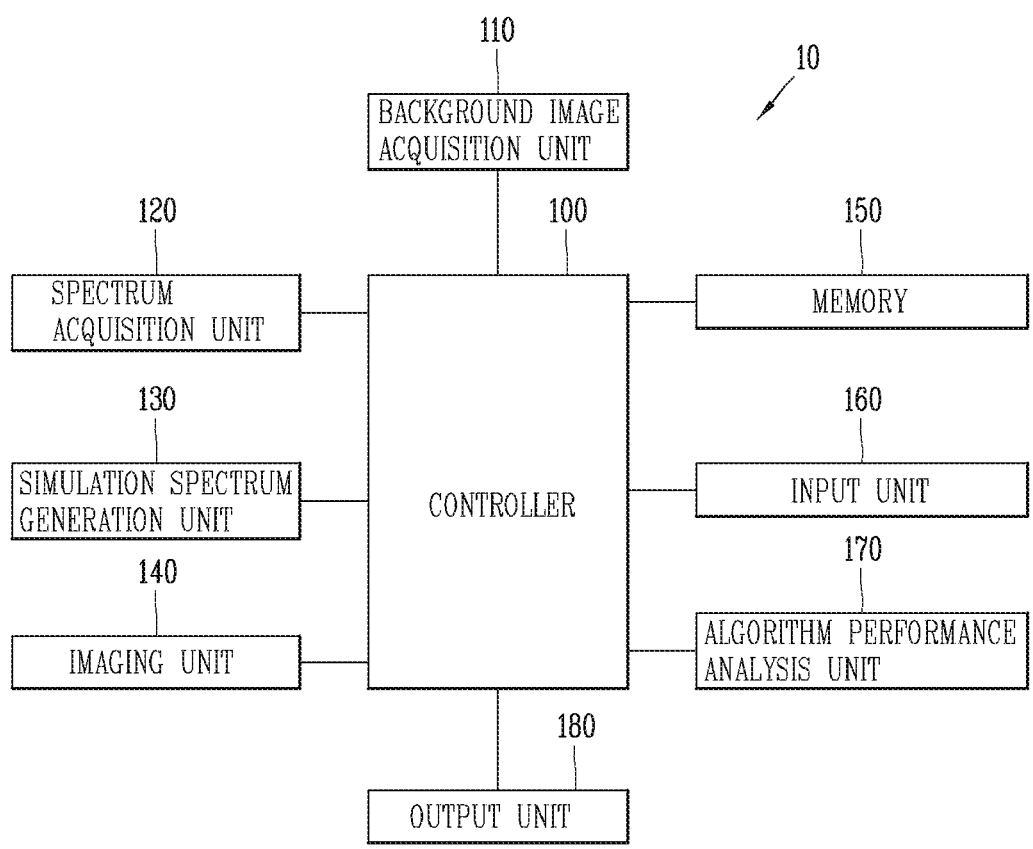
FIG. 1 is a diagram for describing a configuration of a spectrum simulation apparatus according to an embodiment of the present disclosure.
Figure 2:
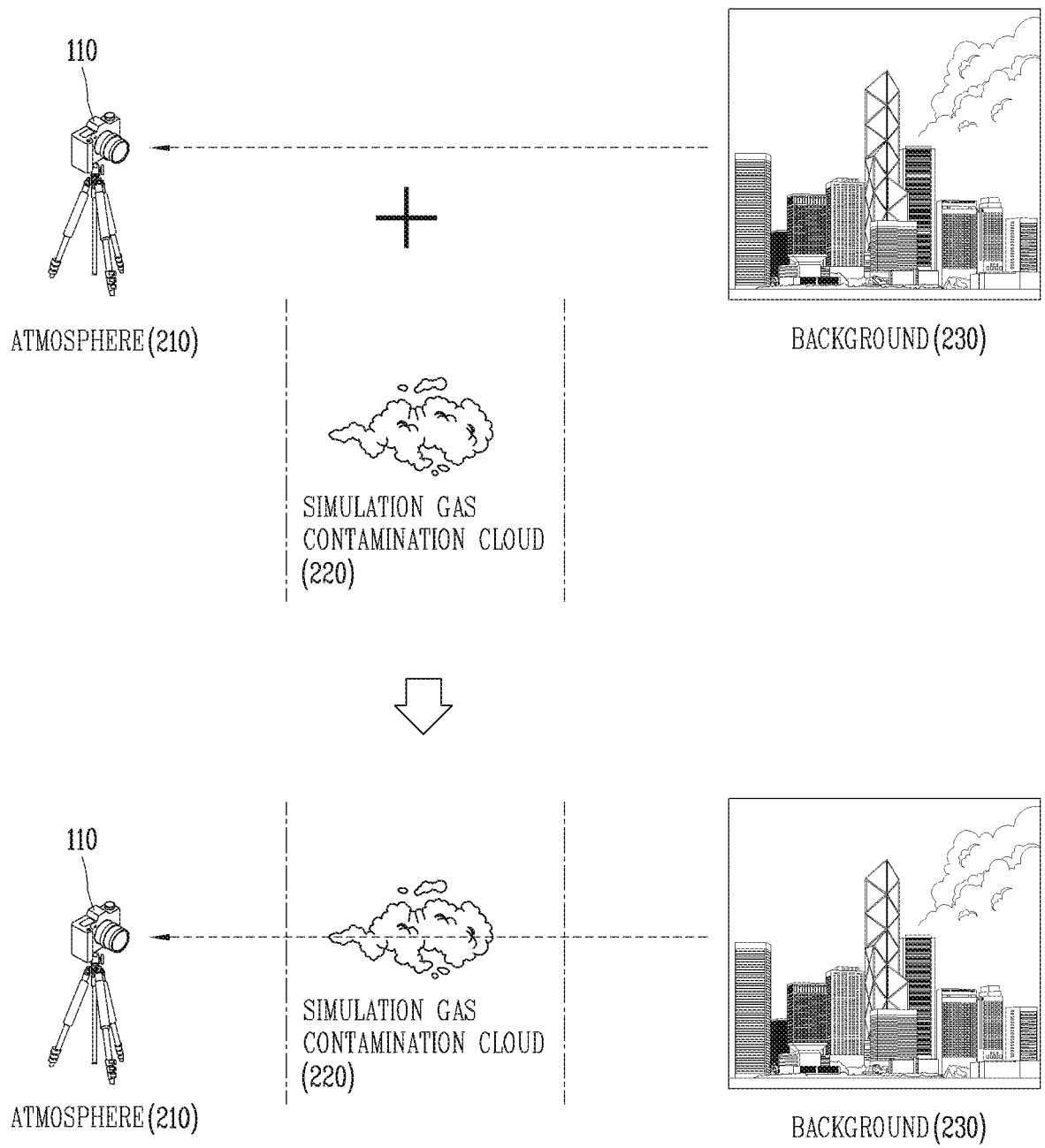
FIG. 2 is a conceptual diagram illustrating a three-layer radiance intensity spectrum model for generating an atmosphere transmittance spectrum of a contamination layer in the spectrum simulation apparatus according to the embodiment of the present disclosure.

First, FIG. 1 is a block diagram for describing a configuration of the spectrum simulation apparatus according to the embodiment of the present disclosure. Then, FIG. 2 is a conceptual diagram illustrating a three-layers radiation intensity spectrum model for generating an atmosphere transmittance spectrum of a contamination layer in the spectrum simulation apparatus according to the embodiment of the present disclosure.

First, with reference to FIG. 1, a spectrum simulation apparatus 10 according to an embodiment of the present disclosure is configured to include a controller 100, and a background image acquisition unit 110, a spectrum acquisition unit 120, a simulation spectrum generation unit 130, an imaging unit 140, a memory 150, an input unit 160, and an algorithm performance analysis unit 170, which are connected to the controller 100. Then, the spectrum simulation apparatus 10 may further include an output unit 180.

First, the background image acquisition unit 110 acquires a background image. To this end, the background image acquisition unit 110 includes at least one camera for acquiring a background image of a target region. The target region here means a region that is to be a background of the simulated spectrum, as a region in which toxic substance distribution is to be simulated through the spectrum simulation apparatus 10 according to the embodiment of the present disclosure.

In addition, the background image acquisition unit 110 acquires an infrared signal for each pixel of the acquired background image. Here, the infrared signal that is acquired is used for generation of a radiation intensity spectrum characteristic in accordance with the background image, that is, of a background radiation intensity spectrum. To this end, the background image acquisition unit 110 includes at least one infrared sensor.

Then, the spectrum acquisition unit 120 acquires an atmospheric (background) radiation intensity spectrum, that is, a data cube. To this end, the spectrum acquisition unit 120 includes an infrared hyper-spectral imaging spectrometer or is connected to separate spectroscopic equipment that is controllable by the controller 100.

Then, the simulation spectrum generation unit 130 performs modeling in accordance with a three layers-based radiation intensity spectrum model on the basis of a background radiation intensity spectrum acquired in the spectrum acquisition unit 120. Then, radiation intensity spectrums for a case where a gas contamination cloud contaminated with a specific toxic substance is present (a radiation intensity spectrum in the form of a linear combination of a background and an agent that is desired to be detected) and for a case where the contamination cloud is not present are modeled on the basis of a result of the modeling, and thus an infrared hyper-spectral imaging simulation spectrum is generated.

On the other hand, for a simulation spectrum acquired in the simulation spectrum generation unit 130, by utilizing a preset imaging technique, the imaging unit 140 generates a spectrum image in accordance with the simulation spectrum, and a simulation contamination cloud image in accordance with the acquired background image and the spectrum image. The spectrum image here is an image that is made up of colors that are decided according to the simulation spectrum for each pixel. In addition, the preset imaging technique is an imaging technique that uses a tristimulus value function.

On the other hand, various pieces of data and programs for operation of the spectrum simulation apparatus 10 according to the embodiment of the present disclosure are stored in the memory 150. In addition, a gas absorption coefficient library in which pieces of information on various toxic substances are stored in the form of a library, and at least one gas detection algorithm and a performance technique program for a chemical gas detection algorithm performance analysis are stored in the memory 150.

Then, the input unit 160 includes a mechanical input unit and a touch-type input unit for inputting pieces of information on gas, concentration, and atmosphere transmittance, which are simulated, from a user. On the other hand, pieces of information on the gas that is desired to be simulated, that is, on the toxic substance that is desired to be simulated, that is, a type of toxic substance, a concentration of a toxic substance, and the like are pieces of information that are stored in the memory 150. In this case, according to user's input through the input unit 160, at least one toxic substance is selected and various pieces of information associated with the selected toxic substance are selected.

On the other hand, the algorithm performance analysis unit 170 performs analysis of performance of multiple different toxic substance detection algorithms, for example, analysis of gas detection accuracy, on the simulation spectrum acquired in the simulation spectrum generation unit 130, that is, the simulation contamination cloud image.

Then, the output unit 180 outputs various pieces of data of the spectrum simulation apparatus 10 according to the embodiment of the present disclosure, under the control of the controller 100. As an example, the output unit 180 outputs the simulation contamination cloud image in such a manner that it is identified visually by the user. Alternatively, a result of analyzing performance of each of the multiple different toxic substance detection algorithms is output in such a manner that the user identifies the result visually. To this end, the output unit 180 includes at least one display unit on which image information is displayable.

On the other hand, the controller 100 controls overall operation of the spectrum simulation apparatus 10 according to the embodiment of the present disclosure. For example, the controller 100 controls operation of each of the connected constituent elements and the order in which constituent elements operate, and, on the basis of information that is input through the input unit 160, controls each of the connected constituent elements.

For example, through the input unit 160, the user selects at least one from among the toxic substances stored in the standard library for the controller 100. In addition, arbitrary concentration information and atmosphere transmittance information on a chemical agent that is desired to be simulated are input from the user, and the simulation spectrum in accordance with the atmosphere contaminated with a subject-to-simulation chemical agent is generated on the basis of the pieces of information that are input.

FIG. 2 illustrates this process.

With reference to FIG. 2, first, the background image acquisition unit 110 acquires the background image. In this case, according to the three-layers radiation intensity spectrum model, a spectroscopic signal including spectrum characteristics of an atmospheric layer 210 and a background layer 230 is acquired. In this state, a simulation spectrum signal that includes spectrum characteristics of three layers, an atmosphere 210, a gas contamination cloud 220, and a background 230, is generated, reflecting a spectrum characteristic of the gas contamination cloud 220 in accordance with the arbitrary concentration information and atmosphere transmittance information on the chemical agent, which are input by the user.

On the other hand, the simulation spectrum is generated for each pixel of an image acquired in the background image acquisition unit 110. Then, the controller 100 decides a color in accordance with the simulation spectrum generated for each pixel and generates an image that is made up of colors decided according to the simulation spectrum, that is, the simulation spectrum image. Then, the simulation spectrum image is combined with the background image acquired in the background image acquisition unit 110, and thus the simulation contamination cloud image is generated. Then, the output unit 180 is controlled to output the generated simulation contamination cloud image. In addition, the controller 100 acquires a result of detection in accordance with a subject-to-detection algorithm that is reset for the generated simulation spectrum. Then, a contamination cloud image corresponding to the acquired result of the detection is acquired by controlling the imaging unit 140. Then, the acquired contamination cloud image and the simulation contamination cloud image that is generated according to the simulation spectrum are compared, and thus toxic substance detection performance of the subject-to-detection algorithm is analyzed. Then, a result of the analysis is output through the output unit 180.

Figure 3:
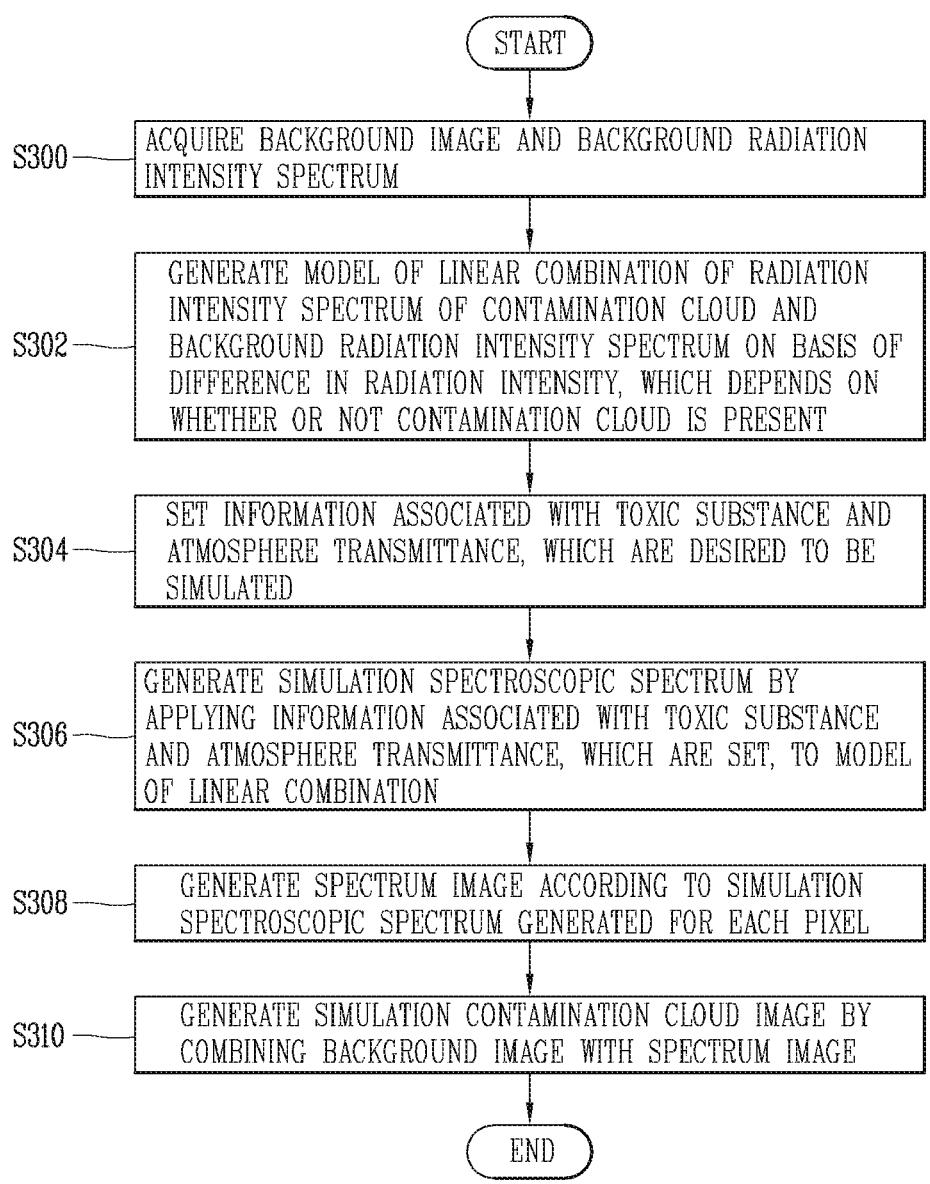
FIG. 3 is a flowchart illustrating an operating process of generating a simulation contamination cloud image in the spectrum simulation apparatus according to the embodiment of the present disclosure.

FIG. 3 is a flowchart illustrating an operating process of generating the simulation contamination cloud image in the spectrum simulation apparatus 10 according to the embodiment of the present disclosure.

With reference to FIG. 3, the spectrum simulation apparatus 10 according to the embodiment of the present disclosure acquires the background image and the infrared signal for each pixel that makes up the background image, by controlling the background image acquisition unit 110, and acquires the background radiation intensity spectrum.

Then, the controller 100 generates a model of a linear combination of a radiation intensity spectrum of a contamination cloud and the background radiation intensity spectrum, on the basis of a difference in radiation intensity, which depends on whether or not the contamination cloud, that is, the atmosphere contaminated with the toxic substance, is present.

To this end, the controller 100 models spectrum information acquired by the spectrum acquisition unit 120, according to the three layers-based radiation intensity spectrum model.

As an example, with reference to FIG. 2, the three-layers radiation intensity spectrum model, according to the spectrum characteristics measured in the infrared hyper-spectral imaging spectrometer, are categorized into three layers, the atmosphere 210, the gas contamination cloud 220, and the background 230.

Here, if physical and chemical properties of each layer are uniform, radiation in the background reaches the atmosphere through the gas contamination cloud and is measured as radiation intensity through a spectrometer. Main parameters that are used in the three layers-based radiation intensity spectrum model are as follows.

$B(T_i, \lambda)$: black-body radiation intensity at a $\lambda$ wave number at temperature T in an i-th layer $L_i(\lambda)$: radiation intensity spectrum at the $\lambda$ wave number in the i-th layer $\tau_i(\lambda)$: Atmosphere transmittance at the $\lambda$ wave number in the i-th layer Here, a relationship between $B(T_i, \lambda)$ and $L_i(\lambda)$ is as in Equation 1.

$$L_i(\lambda) = (1 - \tau_i(\lambda)) B(T_i, \lambda) \qquad \text{Equation 1}$$

That is, the simulation spectrum generation unit 130 models the radiation intensity spectrum acquired in the spectrum acquisition unit 120 into the radiation intensity spectrum of each layer on the basis of Equation 1.

Then, the controller 100 models the radiation intensity spectrum for a case where the contamination cloud contaminated with the toxic substance is present and the radiation intensity spectrum for a case where the contamination cloud is not preset, on the basis of the generated three layers-based radiation intensity spectrum model.

First, in the case where the contamination cloud is not present, a radiation intensity spectrum $L_{off}(\lambda)$ that is acquirable in the spectrum acquisition unit 120 is a spectrum that results from combining the radiation intensity of the background 230, which is reduced to a fixed level due to the atmosphere transmittance of the atmospheric layer 210, and the radiation intensity of the atmospheric layer 210. The radiation intensity spectrum $L_{off}(\lambda)$ for the case where the contamination cloud is not present is expressed as in Equation 2.

$$L_{off}(\lambda) = L_1(\lambda) + \tau_1(\lambda) L_3(\lambda) \quad \text{Equation 2}$$

On the other hand, in the case where a contamination cloud 220 contaminated with the toxic substance is present, light radiated in the background 230 enters the atmospheric layer 210 through the gas contamination cloud 220. Therefore, the radiation intensity of the contamination cloud 220, which is combined with the radiation intensity of the background 230, which is reduced due to the atmosphere transmittance of the contamination cloud 220, is reduced by the atmosphere transmittance of the atmospheric layer 210, and a spectrum results from combining the reduced radiation intensity with the radiation intensity of the atmospheric layer 210. Therefore, a radiation intensity spectrum $L_{on}(\lambda)$ for the case where the contamination cloud is present is expressed as in Equation 3.

$$L_{on}(\lambda) = L_1(\lambda) + \tau_1(\lambda)[L_2(\lambda) + \tau_2(\lambda) L_3(\lambda)] \quad \text{Equation 3}$$

On the other hand, as in Equations 2 and 3, when the radiation intensity spectrum for the case where the contamination cloud is present and the radiation intensity spectrum for the case where the contamination cloud is not present are modeled, a hyper-spectral imaging simulation signal generation unit 130 calculates the radiation intensity spectrum $L_{on}(\lambda)$ for the case where the contamination cloud is present, as in Equation 4, through linear combination.

$$L_{on}(\lambda) = \tau_1(\lambda)(1-\tau_2(\lambda))(B(T_2,\lambda) - L_3(\lambda)) + L_{off}(\lambda) \quad \text{Equation 4}$$

Equation 4 shows the difference in radiation intensity, which depends on whether or not the contamination cloud is present. That is, in Equation 4, $\tau_1(\lambda)(1-\tau_2(\lambda))(B(T_2, \lambda) - L_3(\lambda))$ is a difference in radiation intensity, which is depends on the presence of the contamination cloud. Therefore, in order to detect the contamination cloud in Equation 4, that is, in order not to establish $L_{on} = L_{off}$, $B(T_2,\lambda) - L_3(\lambda) \neq 0$ has to be established.

On the other hand, $L_{on}(\lambda)$ has a non-linear characteristic due to $1-\tau_2(\lambda)$ and $B(T_2,\lambda) - L_3(\lambda)$. Therefore, in Equation 4, non-linear constituent elements $1-\tau_2(\lambda)$ and $B(T_2,\lambda) - L_3(\lambda)$, which results from excluding the atmosphere transmittance $\tau_1(\lambda)$ of the atmospheric layer 210 from the difference in radiation intensity, that is, $\tau_1(\lambda)(1-\tau_2(\lambda))(B(T_2, \lambda) - L_3(\lambda))$, which depends on the presence of the contamination cloud, are each approximated and are each modeled in the form of a linear combination of the radiation intensity spectrum of the contamination cloud 220 and the radiation intensity spectrum of the background 230.

To this end, an infrared hyper-spectral imaging simulation signal generation unit 130 first models atmosphere transmittance ($\tau_2(\lambda)$) of the contamination cloud into a function as in Equation 5, according to Beer-Lambert Law (the law that states that absorbance is proportional to a concentration of the gas contamination cloud).

$$\tau_2(\lambda) = \exp\left[-\sum_{m=1}^{n} \gamma m^\alpha m(\lambda)\right] \quad \text{Equation 5}$$

wherein n denotes a number of a toxic substance existing in the contamination cloud, $\alpha_m(\lambda)$ denotes an absorption coefficient ($\lambda$) at the corresponding wave number ($m^2 \cdot m^{-1}$), and $\gamma$ m denotes a CL value, that is, the concentration ($mg \cdot m^{-2}$) of the toxic substance.

On the other hand, according to the Talyer approximation method, $1-\exp(-x) \cong x$, and therefore $1-\tau_2(\lambda)$ is approximated as in Equation 6.

$$1 - \tau_2(\lambda) \cong \sum_{m=1}^{n} \gamma m^\alpha m(\lambda) \quad \text{Equation 6}$$

On the other hand, linear approximation that uses a Planck Function is possible according to a difference in temperature between the background 230 and the contamination cloud 220. $B(T_2, \lambda) - L_3(\lambda)$ is linearly approximated according to the Planck Function, as in Equation 7.

$$B(T_2,\lambda) - L_3(\lambda) = C_B \Delta T \quad \text{Equation 7}$$

where $C_B$ denotes a constant independent of temperature and a wave number and $\Delta T$ denotes a change in temperature.

Therefore, the infrared hyper-spectral imaging simulation signal generation unit 130 models the difference in radiation intensity $(\tau_1(\lambda)(1-\tau_2(\lambda))(B(T_2,\lambda)-L_3(\lambda)))$ in Equation 4, which depends on the presence of the contamination cloud, into $$\sum_{m=1}^{n} (C_B \Delta T \gamma m) \tau_1(\lambda) \alpha_m(\lambda)$$

on me basis of Equation 6 and Equation 7.

Therefore, the radiation intensity spectrum $L_{on}(\lambda)$ in Equation 4, which is modeled in the infrared hyper-spectral imaging simulation signal generation unit 130, as in Equation 8, is modeled in the form of a linear combination of a function $$\left(\sum_{m=1}^{n}(C_B \Delta T \gamma_m)\tau_1(\lambda)\alpha_m(\lambda)\right)$$

added due to an influence of the contamination cloud and the background radiation intensity spectrum ($L_{off}(\lambda)$).

$$L_{on}(\lambda) = \sum_{m=1}^{n}(C_B \Delta T \gamma_m)\tau_1(\lambda)\alpha_m(\lambda) + L_{off}(\lambda) \quad \text{Equation 8}$$

where $L_{off}(\lambda) = L_1(\lambda) + \tau_1(\lambda) L_3(\lambda)$.

The radiation intensity ($L_{on}(\lambda)$) that is obtained in this manner is changed to a brightness temperature ($T(\lambda)$) signal that is easy to analyze using inverse conversion (Equation 9) that uses the Planck Function, which is described below.

$$L_{on}(\lambda) = \frac{2hc^2\lambda^3}{\exp\left(\frac{hc\lambda}{kT(\lambda)}\right) - 1} \qquad \text{Equation 9}$$

where parameter h denotes a Planck constant (6.62607004×10$^{-34}$ m² kg/s), c denotes the velocity of light (299,792,458 m/s), and k denotes a Boltzmann constant (1.3806488×10$^{-23}$ J/K).

On the other hand, when the radiation intensity spectrum modelled in the form of a linear combination of the contamination cloud and the background radiation intensity spectrum is modeled as in Equation 8 in Step S302, the controller 100 sets information on a specific toxic substance and atmosphere transmittance (S304).

For example, the use selects at least one from among pieces of information on many toxic substances that are stored in the form of a library in the memory 150, for the controller 100. The standard library is information in the form of a set of unique absorption coefficients of toxic substances that are desired to be detected.

Therefore, in a case where the user selects at least one toxic substance from the standard library through the input unit 160, the controller 100 detects an absorption coefficient of at least one selected toxic substance from the standard library. Then, the user also selects a concentration of at least one toxic substance selected through the input unit 160, for the controller 100. In addition, the user also selects pieces of information on the atmosphere transmittance ($\tau_1(\lambda)$) and the background radiation intensity spectrum ($L_{off}(\lambda)$) through the input unit 160 from the controller 100.

On the other hand, when om Step S304, at least one toxic substance is selected and a concentration of the selected toxic substance and the atmosphere transmittance information are set, on the basis of the number of the selected toxic substances, absorption coefficients and a concentration of each toxic substance, and Equation 8, the controller 100 simulates the radiation intensity spectrum for a case where a currently-selected toxic substance contamination cloud is present, that is, generates the simulation spectrum (S306).

On the other hand, the simulation spectrum that is to be generated in Step S306 is generated for each pixel that makes up the background image. Then, the controller 100 controls the imaging unit 140 and thus images the generated simulation spectrum for each pixel (S308). To this end, the controller 100 uses various imaging techniques. As an example of this imaging technique, a method that uses an average brightness temperature spectrum, a tristimulus value method, or the like is used.

For example, the controller 100 performs a change from the radiation intensity spectrum ($L_{on}(\lambda)$) to a brightness temperature spectrum ($T(\lambda)$) on the basis of Equation 9. Then, brightness temperature spectrums obtained for each pixel are integrated, and thus average brightness temperature μ is obtained as follows $$\mu = \frac{1}{p}\sum_{i=1}^{p} x_i \qquad \text{Equation 10}$$

wherein $x_i$ denotes a response of i-th band in the brightness temperature spectrum and p denotes the number of spectrum bands. This value μ may be normalized and may be mapped to a value from 0 to 255 for configuring a black and white image or may be mapped to a value from 0 to 1023 for configuring a color image. Accordingly, a color in accordance with the simulation spectrum is decided for each pixel, and, as a result of performing Step S308, the spectrum image in which colors are decided according to the simulation spectrum for each pixel is generated.

Still another imaging technique is a method that uses the tristimulus value function. Generally, the tristimulus value function means a function that is defined in a visible light band from 380 to 750 nm. Step S308 of imaging the simulation spectrum for each pixel according to the tristimulus value function will be described in more detail below with reference to FIG. 4.

On the other hand, when, in Step S308, the simulation spectrum for each pixel is imaged and thus the spectrum image is generated, the controller 100 combines the generated spectrum image and the background image and thus generates the simulation contamination cloud image (S310).

In this case, in the simulation contamination cloud image, a region that is contaminated with the toxic substance in the background image is displayed differently than a region that is not contaminated, and two regions, although contaminated with the same toxic substance, are displayed differently in a case where they are different in concentration. Accordingly, a state where the atmosphere is contaminated is visually, through the simulation contamination cloud image, in the simulation contamination cloud image.

Figure 4:
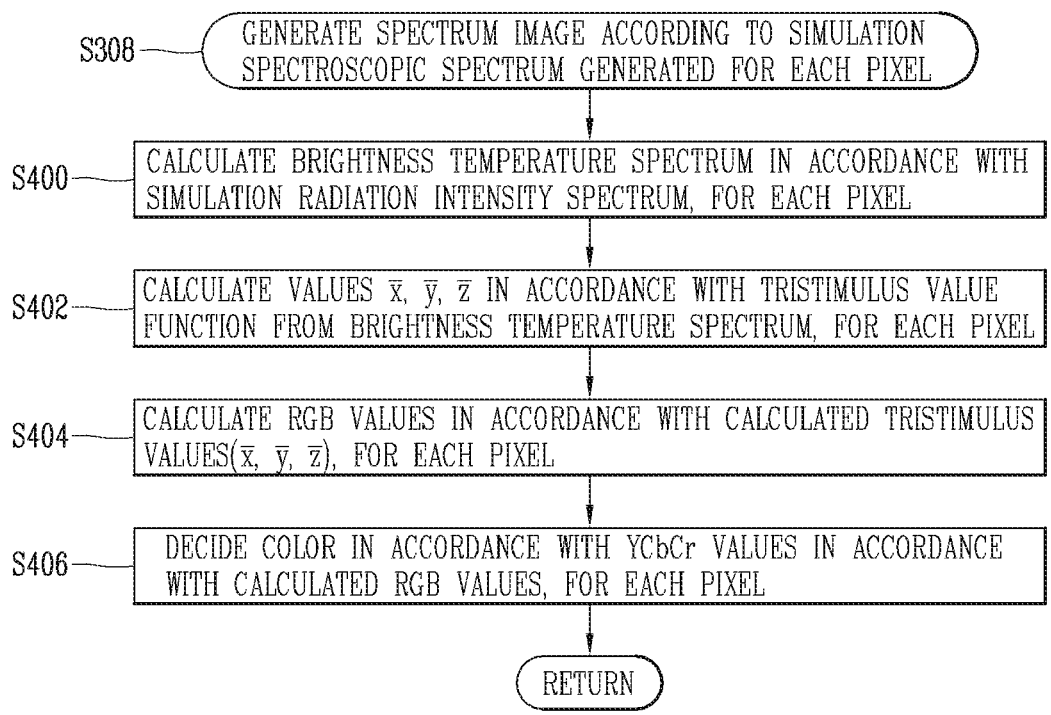
FIG. 4 is a flowchart illustrating in more detail an operating step of generating a spectrum image in the operating process in FIG. 3.

On the other hand, FIG. 4 is a flowchart illustrating in more detail an operating step of generating the spectrum image, in the operating process in FIG. 3. FIG. 5 is a diagram illustrating examples of the tristimulus value function for generating the simulation contamination cloud image in the spectrum simulation apparatus 10 according to the embodiment of the present disclosure.

With reference to FIG. 4, the controller 100 first calculates the brightness temperature spectrum ($T(\lambda)$) from a simulation radiation intensity spectrum ($L_{on}(\lambda)$) that is generated for each pixel according to a relationship in Equation 9 (S400).

Then, values $\bar{x}$, $\bar{y}$, $\bar{z}$ in accordance with the tristimulus value function are calculated from the brightness temperature spectrum calculated for each pixel (S402).

According to the present disclosure, in using this for hyper-spectral imaging remote-distance gas detection, the tristimulus value function is defined as illustrated in FIG. 5B, in such a manner that a region range is suitable for a band from 7 to 14 μm. As is the case with k that is illustrated in FIGS. 5A and 5B, simulation in typical three specific bands is possible with a CIE 1931 standard tristimulus value function.

According to the present disclosure, the three specific bands are as follows: a band of 950 to 1100 cm$^{-1}$ in which absorption properties of ozone appear, a band of 1200 to 1450 cm$^{-1}$ in which absorption properties of water vapor are distributed widely, and a band of 1100 to 1200 cm$^{-1}$ in which narrowband absorption properties of other substances appear and influences of water vapor and ozone are comparatively small. Each of the tristimulus value functions ($\bar{x}(\lambda)$, $\bar{y}(\lambda)$, $\bar{z}(\lambda)$) is possibly expressed as a Gaussian function ($ae^{-(x-b)^2/c^2}$).

Here, a, b, and c are constant values and are defined differently according to a resolution of a hyper-spectral imaging acquisition apparatus and a characteristic thereof. Then, a value of the tristimulus value function is obtained from the calculated brightness temperature spectrum, as in Equation 11.

$$X = \int_\lambda^p \bar{x}(\lambda)T(\lambda)d\lambda = \sum_\lambda \bar{x}(\lambda)T(\lambda)$$
$$Y = \int_\lambda^p \bar{y}(\lambda)T(\lambda)d\lambda = \sum_\lambda \bar{y}(\lambda)T(\lambda)$$
$$Z = \int_\lambda^p \bar{z}(\lambda)T(\lambda)d\lambda = \sum_\lambda \bar{z}(\lambda)T(\lambda)$$

Equation 11 where R, G, and B values are substituted for values ($\bar{x}, \bar{y}, \bar{z}$) of the tristimulus value function through Equation 12 (S404).

$$\begin{bmatrix} R \\ G \\ B \end{bmatrix} = \begin{bmatrix} 2.36353918 & -0.51511248 & 0.00524373 \\ -0.89582361 & 1.42643694 & -0.01452082 \\ -0.46771557 & 0.08867553 & 1.00927709 \end{bmatrix} \begin{bmatrix} X \\ Y \\ Z \end{bmatrix}$$

Equation 12

On the other hand, the controller 100 performs a change to YCbCr color spaces for separating acquired R, G, and B color codes back into a brightness signal (luminosity) and color information (S406). For example, Step S406 is performed through the use of Equation 13.

$$[Y\ Cb\ Cr] = [R\ G\ B] * C$$
$$C = \begin{bmatrix} 0.299 & 0.168935 & 0.499813 \\ 0.587 & -0.331665 & -0.418531 \\ 0.114 & 0.50059 & -0.081282 \end{bmatrix}$$

Equation 13

Accordingly, the spectrum simulation apparatus 10 according to the embodiment of the present disclosure acquires a YCbCr color value for each pixel and generates the spectrum image that is configured with pixels having acquired colors.

Then, in Step S310 in FIG. 3, the controller 100 synthesizes the spectrum image and the background image and thus generates the simulation contamination cloud image. FIGS. 6A and 6B illustrate an example of the simulation contamination cloud and examples of a radiation intensity spectrum 610 of the background and a simulated spectrum 600 of the toxic substance, respectively.

On the other hand, the spectrum simulation apparatus 10 according to the embodiment of the present disclosure utilizes the simulation contamination cloud image generated according to the present disclosure and thus compares and analyzes performance of multiple toxic substance detection algorithms.

Figure 7:
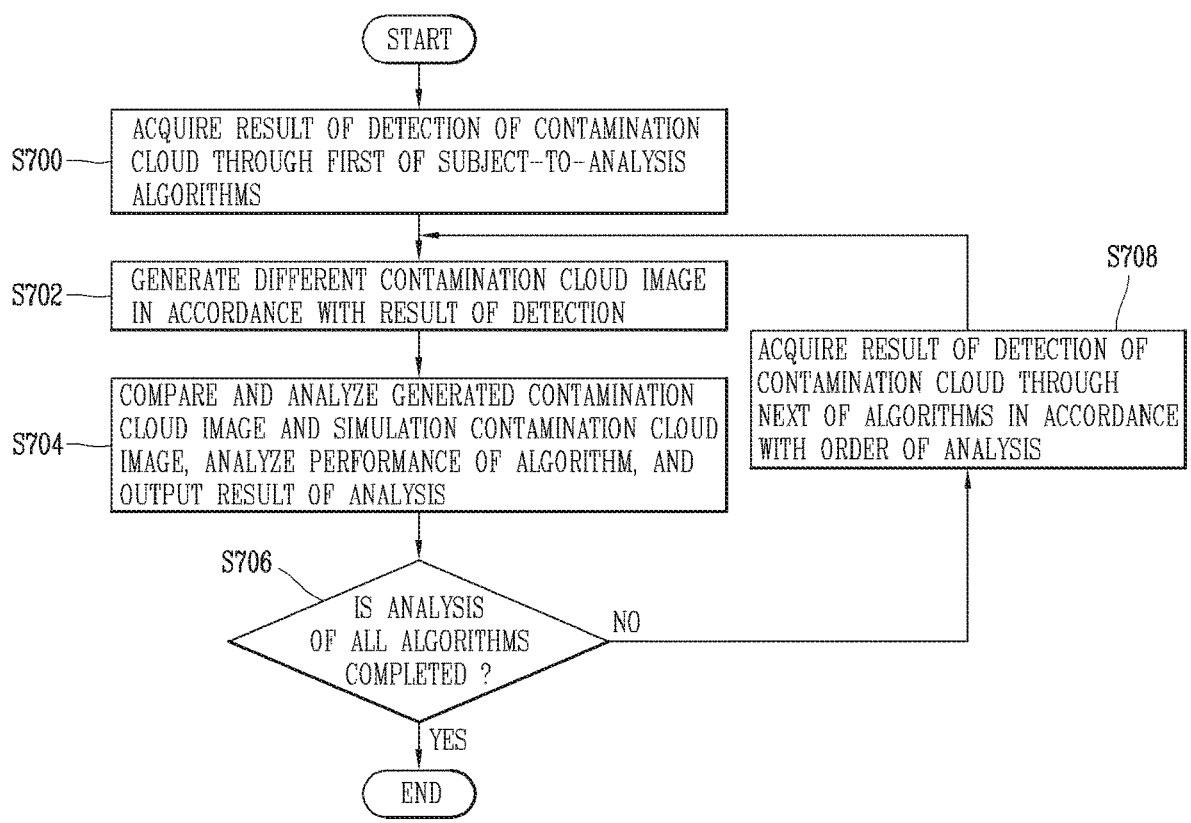
FIG. 7 is a flowchart illustrating an operating process of analyzing performance of a different detection algorithm on the basis of the simulated contamination cloud image in the spectrum simulation apparatus according to the embodiment of the present disclosure.
Figure 8:
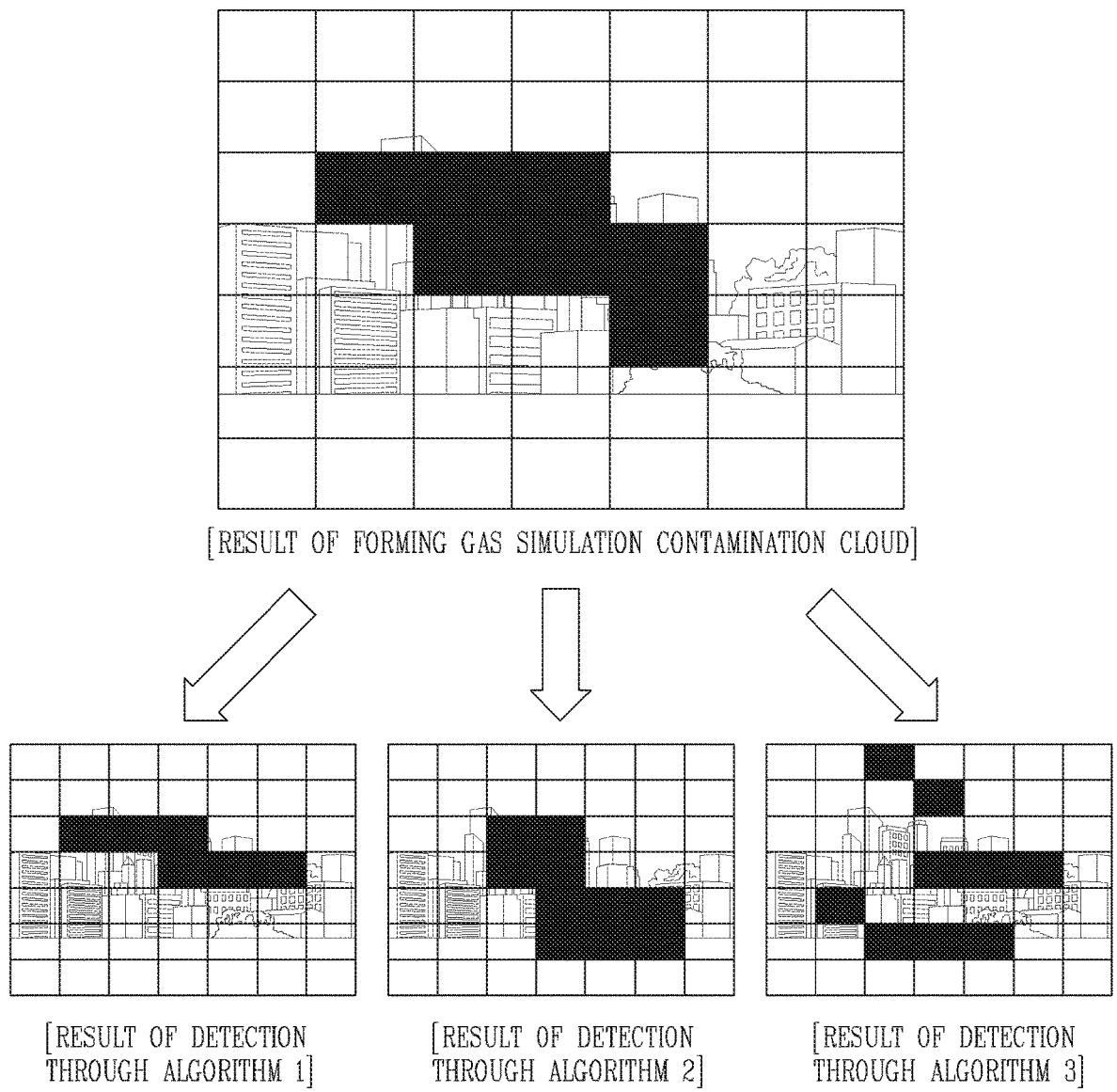
FIGS. 8 and 9 are diagrams each illustrating an example in which different detection algorithms are compared and analyzed, in terms of performance, according to the operating process in FIG. 7.
Figure 9:
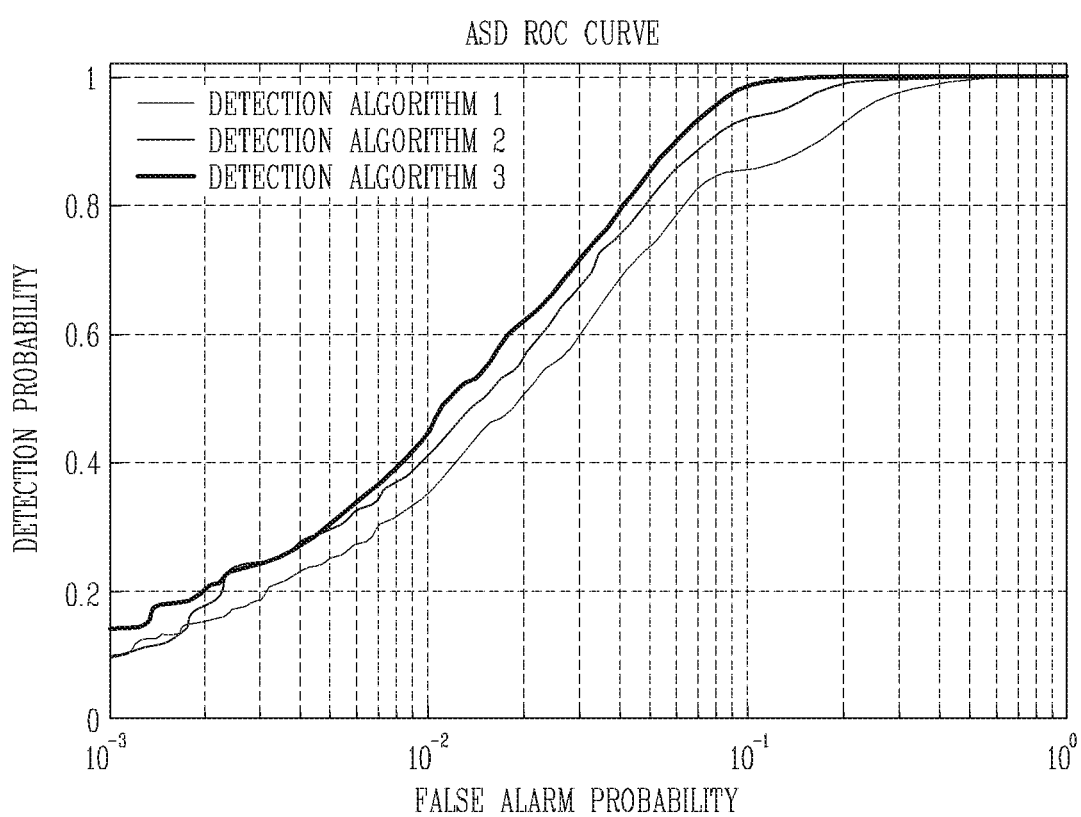

FIG. 7 is a flowchart illustrating an operating process of analyzing performance of a different detection algorithm on the basis of the simulated contamination cloud image in the spectrum simulation apparatus 10 according to the embodiment of the present disclosure. Then, FIGS. 8 and 9 are diagrams each illustrating an example in which different detection algorithms are compared and analyzed, in terms of performance, according to the operating process in FIG. 7.

First, with reference to FIG. 7, the controller 100 of the spectrum simulation apparatus 10 according to the embodiment of the present disclosure acquires a result of the detection in accordance with the first of multiple subject-to-analysis algorithms, with respect to a currently-simulated spectrum, that is, a contamination cloud image. To this end, the algorithm performance analysis unit 170 employs a configuration in which toxic substance detection is performed in accordance with the subject-to-analysis algorithm. As an example, an image (an image for a spectroscopic spectrum analysis, for example, an infrared image) that results from imaging a target region is input, as an image of a current contamination cloud, in the algorithm performance analysis unit 170, and the algorithm performance analysis unit 170 detects the toxic substance detection in accordance with the currently-selected subject-to-detection algorithm, from the image that is input.

On the other hand, the result of the detection is determined for each pixel of the image that is input. As an example, with the result of the detection, the presence or absence of, and the concentration of, a specific toxic substance, and the like are determined. Then, the controller 100 images the result of the detection for each pixel through the imaging unit 140 and thus generates the contamination cloud image in accordance with the currently-selected subject-to-analysis algorithm (S702). As an example, the imaging unit 140 generates the contamination cloud image corresponding to the image that is input, on the basis of the result of the detection for each pixel.

When the contamination cloud image in accordance with the result of the detection through the subject-to-analysis algorithm is generated, the controller 100 compares and analyzes the generated contamination cloud image, and the contamination cloud image in accordance with the currently-generated simulation spectrum, that is, the image that is input. Then, as the result of the analysis, a result of quantifying performance of the currently-selected subject-to-analysis algorithm is output (S704). FIGS. 8 and 9 are diagrams each illustrating an example in which a result of comparing and analyzing performance of multiple subject-to-analysis algorithms is output.

As an example, as illustrated in FIG. 8, with respect to pixels of the contamination cloud image in accordance with the simulation spectrum, on which the toxic substance is present, the controller 100 quantifies the performance of the currently-selected subject-to-analysis algorithm on the basis of a ratio among pixels of the contamination cloud image in accordance with the result of the detection through the subject-to-analysis algorithm, from which the toxic substance is detected. That is, with respect to the total number of pixels of the contamination cloud image in accordance with the simulation spectrum, the number of pixels of the contamination cloud image in accordance with the result of the detection through the subject-to-analysis algorithm, which are matched, in terms of the result of the detection of the toxic substance (for example, in terms of the presence or absence of the toxic substance), with pixels of the contamination cloud image in accordance with the simulation spectrum is the quantified performance of the subject-to-analysis algorithm.

Alternatively, the controller 100 quantitively analyzes the performance of the subject-to-analysis algorithm through a preset analysis algorithm. As an example of this analysis algorithm, as illustrated in FIG. 9, a receiver operating characteristic (ROC) analysis technique that considers erroneous detection (false alarm) is used. There are advantages in that the ROC analysis technique is possibly utilized for comparing and improving the performance of the detection algorithm in developing a remote-distance chemical imaging detection technology and in that, with the ROC analysis technique, simulation detection testing is possible without having to perform direct injection.

On the other hand, when the quantified performance of the currently-selected subject-to-analysis algorithm is analyzed and output, the controller 100 determines whether or not all multiple subject-to-analysis algorithms are analyzed (S706). Then, in a case where all multiple subject-to-analysis algorithms are not analyzed, the next of the multiple subject-to-analysis algorithms is selected according to the order of analysis, and, through the algorithm performance analysis unit 170, a currently-simulated contamination cloud image input into the next algorithm according to the order of analysis and a result of the detection is accordingly acquired (S708). Then, Steps S702 and S704 in which the contamination cloud image is acquired from the result of the detection acquired from the currently-selected subject-to-analysis algorithm and in which the quantified performance of the currently-selected subject-to-analysis algorithm is analyzed from the acquired contamination cloud image are performed repeatedly.

On the other hand, in Step S706, in a case where all multiple subject-to-analysis algorithms are analyzed, the controller 100 ends the operating process of quantitatively analyzing the performance of the subject-to-analysis algorithm, which is illustrated in FIG. 7.

On the other hand, the specific embodiments of the present disclosure are described above, but various modifications to the specific embodiments are possibly implemented without departing from the scope of the present disclosure. For example, according to the present disclosure, of course, a simulation spectroscopic signal for a contamination cloud including many toxic substances, for example, multiple agents, not one toxic substance, may be generated.

On the other hand, according to the present disclosure, as an example, the simulation contamination cloud image is described above as being generated with the YCbCr values, and this is for making the image more definitely. However, of course, the image of the simulation contamination cloud may be generated as a white and color image on the basis of an average brightness temperature, or a color of the simulation contamination cloud may be decided according to the RGB value that is available before being converted into the YCbCr value. In this case, the process of performing conversion into the YCbCr value is not included, and therefore, the simulation contamination image is generated at a higher speed. However, the degree of sharpness decreases more than when an image is generated according to the YCbCr value.

The present disclosure can be implemented as computer-readable codes in a program-recorded medium. The computer-readable medium may include all types of recording devices each storing data readable by a computer system. Examples of such computer-readable media may include hard disk drive (HDD), solid state disk (SSD), silicon disk drive (SDD), ROM, RAM, CD-ROM, magnetic tape, floppy disk, optical data storage element and the like. Also, the computer-readable medium may also be implemented as a format of carrier wave (e.g., transmission via an Internet). The computer may include the controller.

It will be understood by those skilled in the art that various changes and modifications may be made without departing from the spirit and scope of the disclosure as defined by the appended claims. Therefore, it should also be understood that the above-described embodiments are not limited by any of the details of the foregoing description, unless otherwise specified, but rather should be construed broadly within its scope as defined in the appended claims. The scope of the present disclosure should be determined by rational interpretation of the appended claims, and all changes within the scope of equivalents of the present disclosure are included in the scope of the present disclosure.

What is claimed is:

1. A spectrum simulation apparatus using virtual information on at least one toxic substance generated by a user comprising:
    a background image acquisition unit including at least one camera and an infrared sensor configured to acquire a background image of a target region and an infrared signal corresponding to each pixel of the background image;
    a spectrum acquisition unit configured to acquire a background radiation intensity spectrum from the infrared signal acquired for the each pixel;
    an input unit configured to input, by a user, the virtual information on at least one toxic substance and atmosphere transmittance that are generated by the user;
    a simulation spectrum generation unit configured to generate a model of a linear combination of a radiation intensity spectrum of a contamination cloud and a background radiation intensity spectrum on the basis of a difference in radiation intensity, which depends on whether or not the contamination cloud is present;
    a controller configured to control the simulation spectrum generation unit in such a manner that a simulation spectrum of the contamination cloud contaminated with the at least one toxic substance, which corresponds to the each pixel, is generated by applying the virtual information on the at least one toxic substance and the atmosphere transmittance that are generated by the user to the model of the linear combination; and
    an imaging unit that, under the control of the controller, configured to generate a spectrum image in accordance with the simulation spectrum corresponding to the each pixel, combines the generated spectrum image and the background image, and thus generates a simulation contamination cloud image.

2. The spectrum simulation apparatus of claim 1,
    wherein the simulation spectrum generation unit is further configured to make division into three phases, including an atmosphere, a contamination cloud, and a background, and, on the basis of a three layers-based spectrum model that models a spectroscopic signal and the acquired background radiation intensity spectrum, models a first spectrum model for a case where the contamination cloud is present and a second spectrum model for a case where the contamination cloud is not present, and
    wherein the simulation spectrum generation unit is further configured to linearly combine a result of approximating a contamination cloud function, which results from approximating the atmosphere transmittance of the contamination cloud using a preset approximation method, and a difference between black-body radiation intensity of the contamination cloud and radiation intensity of the background, and the second spectrum model, and thus generates the model of the linear combination.

3. The spectrum simulation apparatus of claim 1,
    wherein the imaging unit is further configured to calculate a brightness temperature spectrum on the basis of the simulation spectrum corresponding to each pixel, decides a color value for each pixel according to the calculated brightness temperature spectrum, and thus generates the spectrum image.

4. The spectrum simulation apparatus of claim 3,
wherein the imaging unit is further configured to calculate a tristimulus value for the brightness temperature spectrum calculated for each pixel according to a tristimulus function, calculates a RGB value for each pixel according to the calculated tristimulus value, and generates the spectrum image in which a color of each pixel is decided according to the calculated RGB value.

5. The spectrum simulation apparatus of claim 4,
wherein the imaging unit is further configured to calculate a YCbCR value corresponding to the RGB value calculated for each pixel and generates the spectrum image in which the color of each pixel is decided according to the calculated YCbCR value.

6. The spectrum simulation apparatus of claim 1, further comprising:
a memory storing pieces of information on multiple detection algorithms; and
an algorithm performance analysis unit configured to perform toxic substance detection for each of the multiple detection algorithms on the generated simulation cloud image under the control of the controller.

7. The spectrum simulation apparatus of claim 6,
wherein, when at least one of the multiple detection algorithms is selected, the controller is further configured to control the algorithm performance analysis unit in such a manner that the generated simulation contamination cloud image is input into the selected detection algorithm and that a result of toxic substance detection in accordance with the selected algorithm is derived, and
wherein the controller is further configured to control the imaging unit to image the result of the toxic substance detection, perform comparison with the imaged result of the toxic substance detection, and analyze performance of the selected detection algorithm.

8. The spectrum simulation apparatus of claim 6, further comprising:
an output unit configured to output the simulation contamination cloud image that results from the imaging in the imaging unit, or an imaged result of the toxic substance detection through the detection algorithm, as visual information.

9. The spectrum simulation apparatus of claim 1,
wherein, with respect to the total number of pixels of the simulation contamination cloud image, the controller is further configured to analyze quantified performance of the selected detection algorithm according to the number of pixels in an imaged result of toxic substance detection, which are matched, in terms of the presence or absence of the toxic substance, with pixels of the simulation contamination cloud image.

10. The spectrum simulation apparatus of claim 1,
wherein the controller is further configured to analyze performance of the detection algorithm on the basis of an imaged result of toxic substance detection, and a receiver operating characteristic (ROC) analysis technique for the simulation contamination cloud image.

11. A spectrum simulation method using virtual information on at least one toxic substance generated by a user comprising:
a first step of including at least one camera and an infrared sensor and acquiring a background image of a target region and an infrared signal corresponding to each pixel of the background image;
a second step of acquiring a background radiation intensity spectrum from the infrared signal acquired for the each pixel;
a third step of generating a model of a linear combination of a radiation intensity spectrum of a contamination cloud and a background radiation intensity spectrum on the basis of a difference in radiation intensity, which depends on whether or not the contamination cloud is present;
a fourth step of generating a simulation spectrum of the contamination cloud contaminated with at least one toxic substance, which corresponds to the each pixel, by applying the virtual information on the at least one toxic substance and atmosphere transmittance to the model of the linear combination, when the virtual information on the at least one toxic substance and the atmosphere transmittance that are generated by the user that are desired to be simulated are input by a user; and
a fifth step of generating a spectrum image in accordance with the simulation spectrum corresponding to the each pixel, combining the generated spectrum image and the background image, and thus generating a simulation contamination cloud image.

12. The spectrum simulation method of claim 11,
wherein the third step includes
a (3-1)-th step of making division into three phases, including an atmosphere, a contamination cloud, and a background and modeling a first spectrum model for a case where the contamination cloud is present and a second spectrum model for a case where the contamination cloud is not present, on the basis of a three layers-based spectrum model that models a spectroscopic signal and the acquired background radiation intensity spectrum; and
a (3-2)-nd step of linearly combining a result of approximating a contamination cloud function, which results from approximating the atmosphere transmittance of the contamination cloud using a preset approximation method, and a difference between black-body radiation intensity of the contamination cloud and radiation intensity of the background, and the second spectrum model and thus generating the model of the linear combination.

13. The spectrum simulation method of claim 11,
wherein, with the spectrum image, a brightness temperature spectrum is calculated on the basis of the simulation spectrum corresponding to each pixel, and a color value for each pixel is decided and generated according to the calculated brightness temperature spectrum.

14. The spectrum simulation method of claim 11, further comprising:
an a step of selecting at least one of preset multiple detection algorithms;
a b step of inputting the generated simulation contamination cloud image into the selected detection algorithm and deriving a result of toxic substance detection in accordance with the selected algorithm;
a c step of imaging the derived result of the toxic substance detection; and
a d step of performing a comparison with the imaged result of the toxic substance detection and analyzing performance of the selected detection algorithm.

15. The spectrum simulation method of claim 14,
wherein the d step is a step of analyzing quantified performance of the selected detection algorithm according to the number of pixels in the imaged result of toxic substance detection, which are matched, in terms of the presence or absence of the toxic substance, with pixels of the simulation contamination cloud image, with respect to the total number of pixels of the simulation contamination cloud image.

16. The spectrum simulation method of claim 14, wherein the d step is a step of analyzing performance of the selected detection algorithm on the basis of the imaged result of the toxic substance detection, and a receiver operating characteristic (ROC) analysis technique for the simulation contamination cloud image.

* * * * *